United States Patent [19]

Franklin

[11] Patent Number: 4,849,561

[45] Date of Patent: * Jul. 18, 1989

[54] LIQUID PHASE PROCESS FOR DEHYDROCHLORINATION OF HALOALKANES IN THE PRESENCE OF AN INITIATOR BASED ON AN ORGANIC CHLORINATED PRODUCT

[75] Inventor: James Franklin, Brussels, Belgium

[73] Assignee: Solvay & Cie (Société Anonyme), Brussels, Belgium

[ * ] Notice: The portion of the term of this patent subsequent to Sep. 23, 2003 has been disclaimed.

[21] Appl. No.: 16,088

[22] Filed: Feb. 18, 1987

[30] Foreign Application Priority Data

Feb. 20, 1986 [BE] Belgium ............................. 0/216285

[51] Int. Cl.$^4$ ............................................. C07C 17/34
[52] U.S. Cl. ..................................... 570/220; 570/228
[58] Field of Search ........................ 570/220, 227, 228

[56] References Cited

U.S. PATENT DOCUMENTS

| | | | |
|---|---|---|---|
| 2,593,451 | 4/1952 | Hill et al. . | |
| 3,240,834 | 3/1966 | Kruse et al. .......................... | 570/227 |
| 4,613,709 | 4/1986 | Franklin .............................. | 570/227 |

FOREIGN PATENT DOCUMENTS

| | | |
|---|---|---|
| 904251 | 8/1986 | Belgium . |
| 133690 | 8/1984 | European Pat. Off. . |
| 172596 | 2/1986 | European Pat. Off. . |
| 573532 | 11/1948 | United Kingdom . |

*Primary Examiner*—Howard T. Mars
*Attorney, Agent, or Firm*—Spencer & Frank

[57] ABSTRACT

The liquid phase dehydrochlorination of haloalkanes is performed with an initiator mainly comprising decachlorobutane and/or octachloro-1-butene.

The process is applicable, in particular, to the production of chloroethylenes from the corresponding polychloroethanes.

10 Claims, No Drawings

LIQUID PHASE PROCESS FOR DEHYDROCHLORINATION OF HALOALKANES IN THE PRESENCE OF AN INITIATOR BASED ON AN ORGANIC CHLORINATED PRODUCT

The present invention relates to a liquid phase process for dehydrochlorination of haloalkanes such as tetrachloroethanes in the presence of an initiator based on an organic chlorinated product.

It is known from French Pat. No. 947,324 that the pyrolytic dehydrochlorination of haloalkanes in the vapour phase, in particular of dichloroethane, tetrachloroethane, 1,1,2-trichloroethane and dichloropropane, can be catalysed or initiated by the addition of small amounts of chlorine or of a substance which provides chlorine at a high temperature, for example hexachloroethane.

It is also known from European patent application A1-No.0,133,690 that the pyrolytic dehydrochlorination of 1,2-dichloroethane can be performed in the gaseous phase at between 300 and 600° C. at atmospheric pressure or under a higher pressure in the presence of compounds containing 3 carbon atoms and at least 6 chlorine atoms.

These known processes are performed in the gaseous phase or in the vapour phase, and possess all the disadvantages inherent in pyrolytic reactions. In effect, all the chlorinated hydrocarbons known as initiators lead, below 350° C., to only small degrees of pyrolysis. To increase these degrees of pyrolysis, it is necessary to work at high temperature, which consequently increases the energy costs and gives rise to the formation of byproducts and coke; the latter deposits on the walls of the pyrolysis reactor, thereby requiring periodic stopping in order to clean it.

There is hence, to date, no process for dehydrochlorination of haloalkanes performed in the liquid phase in the presence of initiators based on organic chlorinated products which does not still appear to have the disadvantages of the processes carried out in the gaseous phase.

The object of the present invention is to remedy this deficiency by providing a new process for the liquid phase dehydrochlorination of haloalkanes in the presence of initiators based on organic chlorinated products.

To this end, the invention relates to a liquid phase process for dehydrochlorination of haloalkanes in the presence of an initiator based on an organic chlorinated product which mainly comprises decachlorobutane or an octachlorobutene such as octachloro-1-butene and/or a mixture of these products. Preferably, the initiator based on a chlorinated product results from the additive chlorination of hexachloro-1,3-butadiene.

By chlorinated product, there is understood the product or products resulting from the additive chlorination of hexachloro-1,3-butadiene which is capable of being obtained in a manner known per se, for example by photochlorination or by chlorination in the liquid phase catalysed by iron. When the additive chlorination of hexachlorobutadiene leads to the formation of mixtures of products, these mixtures contain, in addition to the principal products mentioned above, a little hexachloroethane and possibly unconverted hexachloro-1,3-butadiene, as well as a small proportion of various other products. When the additive chlorination of hexachlorobutadiene leads to the formation of a single chlorinated product, the latter is generally an octachlorobutene such as octachloro-1-butene or cecachlorobutane.

The production of a mixture of products or of a single chlorinated product depends, in particular, on the degree of chlorination of the hexachlorobutadiene, the temperature and the nature of the catalyst.

It is, however, obvious that, by a mixture of chlorinated products resulting from the additive chlorination of hexachloro-1,3-butadiene, there are understood not only the mixtures derived directly from the chlorination but also the mixtures which have, after the chlorination, undergone certain modifications, such as those resulting from distillation or rectification operations as well as crystallization operations, enabling an enrichment to be obtained in one or other of the constituents of the mixture.

Finally, as regards the single chlorinated product generally derived from the additive chlorination of hexachloro-1,3-butadiene capable of being used in the process of the invention, it is also obvious that its origin is not critical per se for the liquid phase dehydrohalogenation process of the invention, and that the origin of this single product can be any other raw material besides hexachloro-1,3-butadiene.

By way of example, the composition is given below, in g/kg, of two crude mixtures resulting from the photochlorination of hexachloro-1,3-butadiene:

|  | Mixture I | Mixture II |
| --- | --- | --- |
| Octachloro-1-butene | 368 | 202 |
| Decachlorobutane | 438 | 609 |
| Hexachloroethane | 68 | 111 |
| Hexachloro-1,3-butadiene | 119 | 23 |
| Other unidentified products | 7 | 55 |

These crude mixtures of products, and indeed certain constituents of these mixtures, can be used in the process according to the invention, in an amount by weight usually between 0.1 and 20%, and preferably between 0.2 and 10%, relative to the haloalkane subjected to the liquid phase dehydrochlorination. Good results have been obtained with amounts of the Mixture I and the Mixture II in the region of 4% by weight, relative to the haloalkane subjected to the pyrolytic dehydrochlorination.

The initiators based on a chlorinated product used in the process of the invention have a very powerful boosting effect in temperature ranges of the liquid phase between 150° and 350° C., and preferably between 175° and 300° C. Thus, in the case of the liquid phase dehydrochlorination of 1,1,1,2-tetrachloroethane under pressure, advantageous degrees of dehydrochlorination are already obtained with the crude mixtures resulting from the additive chlorination of hexachloro-1,3-butadiene, used in the proportion of 4% by weight relative to the 1,1,1,2-tetrachloroethane at temperatures of 200° C. The degrees of dehydrochlorination increase, of course, with a rise in temperature, but at the cost of the appearance of side reactions which give rise to the formation of undesirable by-products. The process according to the invention hence enables a compromise solution to be selected on the basis of the dehydrochlorination temperature.

A considerably advantage of the process according to the invention consequently resides in the fact that it can be applied in a different reaction phase and requiring lower temperatures than those which can be used in the processes of the prior art. Temperatures of between 150° and 350° C. have given good results for the different haloalkanes studied.

Another advantage of the process according to the invention resides in the fact that it can be operated either at atmospheric pressure or under a higher pressure. It is preferable to work at atmospheric pressure or under a moderate pressure.

By moderate pressure, there are understood pressures below 20 atmospheres (20.4 bars). Good results have been obtained at pressures of between 1 and 15 bars.

The liquid phase process for dehydrochlorination of haloalkanes according to the invention can be applied to a large number of reactions. In particular, without any intended limitation, the following applications may be mentioned: manufacture of vinyl chloride from 1,2-dichloroethane, manufacture of vinylidene chloride and cis-and trans-1,2-dichloroethylene from 1,1,2-trichloroethane, manufacture of trichloroethylene from 1,1,2,2-tetrachloroethane or 1,1,1,2-tetrachloroethane.

According to the case, it is advisable to apply the appropriate pressure and temperature conditions suited to the nature of the haloalkanes used, so as to work in the liquid phase while maintaining the temperature conditions at which the initiators based on a chlorinated product exert an optimal effect.

It has also been found that it may be desirable in some cases, in order to minimize the overheating of the reaction mixture, to perform the liquid phase dehydrochlorination reaction in the presence of additives which act as diluents but which are inert with respect to the reagents and the initiators taking part in the reaction. As additives, aliphatic chlorinated derivatives such as carbon tetrachloride or hexachloro-1,3-butadiene, or inorganic products such as hydrogen chloride or nitrogen, are preferably used. It is preferable to work with carbon tetrachloride or hexachloro-1,3-butadiene.

In general, the halogenated organic additives are added to the reaction medium in the proportion of 1 to 25 moles per mole of haloalkane used.

The process according to the invention can be carried out in any apparatus or any reactor which permits the combination of the operating conditions described above.

The examples which follow are given by way of explanation of the process according to the invention.

Examples 1 and 2R are carried out in a Pyrex laboratory apparatus comprising a 250-cm³ round-bottomed flask surmounted by a reflux condenser cooled with ice-cold water. The top of the condenser is connected to two bubblers placed in series. The first contains 50 cm³ of CCl₄ and enables organic substances possibly present in the gases emerging from the condenser to be absorbed; the second contains 100 cm³ of water, intended to take up the hydrogen chloride formed during the dehydrochlorination.

A flowrate of nitrogen of approximately 12 liters (measured at S.T.P.) per hour is injected into the flask in order to carry the HCl formed to the water bubbler, where it is assayed with respect to time.

EXAMPLE 1

20 g of 1,1,1,2-tetrachloroethane and 180 g of hexachloro-1,3-butadiene are introduced into the 250-cm³ round-bottomed flask. The hexachlorobutadiene acts as a heavy dissolving intermediary, enabling the desired temperature to be attained while working at atmospheric pressure.

1.10 g of initiator (mixture I) which corresponds to 2 mol % ($C_4Cl_8 + C_4Cl_{10}$) relative to the 1,1,1,2-$C_2H_2Cl_4$ used, is then added.

The reaction mixture is brought to boiling. Approximately 15 minutes are required to reach the refluxing temperature, which is 190° C.

The amount of HCl assayed in the water bubbler corresponds to conversions of 1,1,1,2-$C_2H_2Cl_4$ to trichloroethylene of 77 and 93 % after 1 and 2 hours' reaction, respectively.

The only organic product found at the end of the reaction, in addition to the unconverted 1,1,1,2-$C_2H_2Cl_4$, the dissolving intermediary, and the initiator and its decomposition products, is trichloroethylene.

EXAMPLE 2R

This experiment is performed under conditions identical to those of Example 1, except for working without the addition of an initiator. The amount of HCl assayed corresponds to conversions of 1,1,1,2-$C_2H_2Cl_4$ of only 16 and 39 % after 1 and 2 hours' reaction, respectively.

EXAMPLE 3

In this example, the reactions are performed in an electrically heated Hastelloy C agitated autoclave having a volume of 1 liter.

500 cm³ (793 g) of 1,1,2,2-tetrachloroethane are introduced into the autoclave and brought to boiling (200° C.) under an absolute pressure of 3.7 bar, adjusted by means of an automatic valve connected to the gaseous phase of the reactor.

32.7 g of initiator (Mixture II) dissolved in 72 g of 1,1,2,2-tetrachloroethane are introduced rapidly by means of a proportioning pump (time approximately 2 minutes).

The hydrogen chloride evolved during the dehydrochlorination and also the organic substances present in the vapour phase are entrained and emerge through the pressure regulation valve, are allowed to expand to atmospheric pressure, and are directed to a condenser cooled with cold water and a gas/liquid separator. The condensed liquid is retrieved by a proportioning pump and reintroduced into the autoclave. The uncondensed gases are directed to a scrubber sprayed with water in order to take up the HCl, which is assayed periodically in the aqueous phase collected at the bottom of the scrubber, thereby enabling the progress of the dehydrochlorination reaction to be followed.

The amount of initiator used corresponds to 1.83 mol % of ($C_4Cl_8 + C_4Cl_{10}$) relative to the initial 1,1,2,2-tetrachloroethane. After 40 minutes' reaction, the amount of HCl evolved corresponds to a conversion of 1,1,2,2-tetrachloroethane to trichloroethylene of 16 %, and the initial rate of evolution of HCl is 0.08 mol/liter 1,1,2,2-tetrachloroethane/min.

EXAMPLE 4R

This example is carried out under the same working conditions as Example 3 above, but without addition of an initiator.

After 40 minutes' reaction, without initiator, the amount of HCl evolved corresponds to a conversion of 1,1,2,2-tetrachloroethane of only 1.8 %. The initial rate only reaches 0.004 mol HCl/liter 1,1,2,2-tetrachloroethane/min.

EXAMPLE 5 AND 6R

The experiments are performed in the same apparatus as Example 3.

213 cm$^3$ (337 g) of 1,1,2,2-C$_2$H$_2$Cl$_4$ are introduced into the autoclave and brought to boiling (200° C.) under an absolute pressure of 3.7 bars. By means of the proportioning pump, 35.1 g of intiator (Mixture II) dissolved in 32 g of 1,1,2,2-tetrachloroethane are introduced at a regular flowrate over a time period of one hour. In total, 4.6 mol % of (C$_4$Cl$_8$ +C$_4$Cl$_{10}$) is introduced relative to the 1.1.2.2-tetrachloroethane used. When all the initiator is introduced, the amount of HCl evolved corresponds to a conversion of 1,1,2,2-tetrachloroethane to trichloroethylene of 34 % (Example 5).

Working without the addition of an initiator (Example 6R), the conversion reaches only 2.5 % after 1 hour.

What is claimed is:

1. A process for dehydrochlorination of haloalkanes, comprising:
    dehydrochlorinating a haloalkane in the liquid phase and with the participation of an initiator consisting essentially of an organic chlorinated product selected from the group consisting of decachlorobutane, an octachlorobutene and a mixture thereof.

2. The process according to claim 1, wherein the initiator results from the additive chlorination of hexachloro-1,3-butadiene.

3. The process according to claim 1 wherein the liquid phase dehydrochlorination is performed in temperature ranges between 150 and 350° C.

4. The process according to claim 1 wherein the initiator is used in an amount of the order of 4 % of the weight of the halide used.

5. The process according to claim 1, wherein vinyl chloride is manufactured by liquid phase dehydrochlorination of 1,2-dichloroethane.

6. The process according to claim 1, wherein vinylidene chloride is manufactured by liquid phase dehydrochlorination of 1,1,2-trichloroethane.

7. The process according to claim 1, wherein trichloroethylene is manufactured by liquid phase dehydrochlorination of 1,1,2,2-tetrachloroethane or 1,1,1,2-tetrachloroethane.

8. The process according to claim 1, wherein said initiator consists essentially of decachlorobutane.

9. The process according to claim 1, wherein said initiator consists essentially of an octachlorobutene.

10. The process according to claim 9, wherein said octachlorobutene is octochloro-1-butene.

* * * * *